US012576094B2

(12) United States Patent
Schmidt et al.

(10) Patent No.: US 12,576,094 B2
(45) Date of Patent: Mar. 17, 2026

(54) COMBINATION CANNABINOID-PHENYLETHANOID FORMULATION FOR TREATMENT OF INFLAMMATION AND METHODS RELATED THERETO

(71) Applicant: Canole LLC, Shreveport, LA (US)

(72) Inventors: David Bradley Schmidt, Shreveport, LA (US); Alana L. Gray, Keithville, LA (US); David T. Coleman, Keithville, LA (US)

(73) Assignee: Canole LLC, Shreveport, LA (US)

(*) Notice: Subject to any disclaimer, the term of this patent is extended or adjusted under 35 U.S.C. 154(b) by 856 days.

(21) Appl. No.: 17/778,786

(22) PCT Filed: Nov. 20, 2020

(86) PCT No.: PCT/US2020/061655
§ 371 (c)(1),
(2) Date: May 20, 2022

(87) PCT Pub. No.: WO2021/102358
PCT Pub. Date: May 27, 2021

(65) Prior Publication Data

US 2023/0346806 A1 Nov. 2, 2023

Related U.S. Application Data

(60) Provisional application No. 62/938,123, filed on Nov. 20, 2019.

(51) Int. Cl.
*A61K 31/00* (2006.01)
*A61K 31/216* (2006.01)
(Continued)

(52) U.S. Cl.
CPC .......... *A61K 31/658* (2023.05); *A61K 31/216* (2013.01); *A61K 36/3482* (2024.05); *A61P 29/00* (2018.01)

(58) Field of Classification Search
CPC ...... A61K 31/658; A61K 31/216; A61K 9/00; A61K 31/222; A61K 31/352;
(Continued)

(56) References Cited

U.S. PATENT DOCUMENTS

2019/0282513 A1* 9/2019 Yerike .................... A61K 31/08

FOREIGN PATENT DOCUMENTS

WO WO-2017059088 A1 * 4/2017 ........... A61K 31/045
WO WO-2017175126 A1 * 10/2017 ........... A61K 31/192
(Continued)

OTHER PUBLICATIONS

Costa, B., et al., "The non-psychoactive cannabis constituent cannabidiol is an orally effective therapeutic agent in rat chronic inflammatory and neuropathic pain", European Journal of Pharmacology. Feb. 5, 2007; 556(1-3): 75-83. Epub Nov. 10, 2006.
(Continued)

*Primary Examiner* — Deborah D Carr
(74) *Attorney, Agent, or Firm* — DICKINSON WRIGHT PLLC; Kristopher Lance Anderson

(57) ABSTRACT

The present invention describes cannabinoid formulations that combine cannabinoids, such as CBD, with other active agents within the phenylethanoid class of compounds, such as oleocanthal, which, in combination, provide synergistic anti-inflammatory effects. These combination preparations are capable of increasing anti-inflammatory effects when compared to each individual compound alone, and are further capable of delivery through a variety of administration routes.

18 Claims, 2 Drawing Sheets

(51) Int. Cl.
*A61K 36/185* (2006.01)
*A61P 29/00* (2006.01)

(58) Field of Classification Search
CPC ...... A61K 36/185; A61K 45/06; A61K 31/05; A61K 36/63; A61P 29/00; A61P 19/02
See application file for complete search history.

(56) References Cited

FOREIGN PATENT DOCUMENTS

| | | | | |
|---|---|---|---|---|
| WO | WO-2017178937 A1 * | 10/2017 | | A61K 31/192 |
| WO | 2021102358 A1 | 5/2021 | | |

OTHER PUBLICATIONS

Covas, M., et al., "Olive Oil and Cardiovascular Health", J. Cardiovasc. Pharmacol. 2009; 54: 477-482. doi: 10.1097/FJC.0b013e3181c5e7fd.
Ji, H., et al., "Multipotent natural agents to combat Alzheimer's disease. Functional spectrum and structural features", Acta Pharmacol. Sin. 2008;29:143-151. doi: 10.1111/j.1745-7254.2008.00752.x.
Li, W., et al., "Inhibition of tau fibrillization by oleocanthal via reaction with the amino groups of tau", J. Neurochem. 2009;110:1339-1351. doi: 10.1111/j.1471-4159.2009.06224.x.
Peyrot Des Gachons, C., et al., "Unusual Pungency from Extra-Virgin Olive Oil is Attributable to Restricted Spatial Expression of the Receptor of Oleocanthal", J. Neurosci. 2011;31:999-1009. doi: 10.1523/JNEUROSCI.1374-10.2011.
Scotece, M., et al., "Further evidence for the anti-inflammatory activity of oleocanthal: Inhibition of MIP-1cx and IL-6 in J774 macrophages and ATDC5 chondrocytes", Life Sciences 91 (2012) 1229-1235.
Smith, A., et al., "Syntheses of (−)-Oleocanthal, a Natural NSAID Found in Extra Virgin Olive Oil, the (−)-Deacetoxy-Oleuropein Aglycone, and Related Analogues", J. Org. Chem. 2007;72:6891-6900. doi: 10.1021/jo071146k.
Sofi, F., et al., "Adherence to Mediterranean diet and health status: meta-analysis", Br. Med. J. 2008;337:a1344.3. doi: 10.1136/bmj.a1344.
Whalley, B., et al., "Antiseizure properties of cannabidiol (CBD) are attenuated in the absence of transient receptor potential vanilloid 1 (TRPV1) receptors (S53.004)", Neurology Apr. 2018, 90 (15 Supplement) S53.004.
International Searching Authority, International Search Report and Written Opinion for PCT/US2020/061655 mailed on Mar. 4, 2021, 14 pages.
Patent Cooperation Treaty, International Preliminary Report on Patentability for PCT/US2020/061655 mailed on May 17, 2022, 6 pages.

* cited by examiner

COMBINATION CANNABINOID-PHENYLETHANOID FORMULATION FOR TREATMENT OF INFLAMMATION AND METHODS RELATED THERETO

CROSS-REFERENCE TO RELATED APPLICATIONS

This application is a 35 U.S.C § 371 national application of PCT Application No. PCT/US20/61655, filed on Nov. 20, 2020, entitled "Combination Cannabinoid-Phenylethanoid Formulation For Treatment Of Inflammation And Methods Related Thereto", which claims the benefit of United States Provisional Patent Application Ser. No. 62/938,123 filed on Nov. 20, 2019, entitled "Combination Cannabinoid-Phenylethanoid Formulation For Treatment Of Inflammation And Methods Related Thereto," and which patent applications are commonly owned by the owner of the present invention. These patent applications are hereby incorporated by reference in their entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of drug delivery formulations. In particular, the present invention provides for a combination cannabinoid formulation for treatment of inflammation when delivered to a patient.

BACKGROUND

*Cannabis* is an annual, primarily dioecious, flowering herb. The genera *Cannabis* is considered to be monospecific (*Cannabis sativa* L.) which is divided into several subspecies (*C. sativa* subsp. *sativa, C. sativa* subsp. indica, *C. sativa* subsp. *ruderalis, C. sativa* subsp. spontanea, *C. sativa* subsp. *kafiristanca*). However, the chemical and morphological distinctions by which *cannabis* has been split into these subspecies are often not readily discernible, appear to be environmentally modifiable, and vary in a continuous fashion. For most purposes, it will suffice to apply the name *Cannabis sativa* to all *cannabis* plants encountered.

Cannabinoids are chemical compounds found in the *Cannabis* plant that interact with receptors in the brain and body to create various effects. *Cannabis* contains over 400 compounds including over 100 cannabinoids, which are aryl-substituted meroterpenes unique to the plant genus *cannabis*. The pharmacology of most of the cannabinoids is largely unknown but the most potent psychoactive agent, $\Delta^9$-tetrahydrocannabinol ($\Delta^9$-THC, or THC), has been isolated, synthesized and much studied due to its abundance and psychoactive attributes. Other plant-based cannabinoids include $\Delta^9$-tetrahydrocannabinolic acid, $\Delta^8$-THC, cannabigerol, cannabidiolic acid, and cannabidiol (CBD). These and other cannabinoids have additive, synergistic or antagonistic effects with THC and may modify its actions when *cannabis* products are consumed.

Certain cannabinoids have little to no psychoactive effects as compared to THC. In particular, CBD has received significant focus as a wellness option. Benefits of CBD have been described in the literature to include anti-inflammatory effects. However, despite efforts to create effective anti-inflammatory cannabinoid formulations, there remains a need in the art for cannabinoid formulations that have increased efficacy and which are conducive to use with traditional drug delivery methods.

SUMMARY OF THE DISCLOSURE

It is therefore an object of the present invention to provide for cannabinoid formulations that combine CBD with other active agents within the phenylethanoid class of compounds which, in combination, provide synergistic anti-inflammatory effects.

In one aspect of the present invention, a composition is provided for treatment of inflammatory conditions, said composition comprising: at least one cannabinoid; and at least one phenylethanoid, such as oleocanthal; wherein said composition is capable of having anti-inflammatory effects when administered to a patient. In one aspect the molar ratio of the at least one cannabinoid to the at least one phenylethanoid is between 10:1 and 1:10. In another aspect the molar ratio of the at least one cannabinoid and the at least one phenylethanoid is between 5:1 and 1:5. In yet another aspect, the molar ratio of the at least one cannabinoid and the at least one phenylethanoid is substantially 1:1 and preferably 1:1.

It is an object of the present invention to provide a composition is suitable for oral administration, including buccal and sublingual administration. In another aspect the composition is suitable for topical administration. In another aspect, the composition is suitable for mucosal administration. In yet another aspect, said composition is suitable for pulmonary administration. The composition is also suitable for suppository, subcutaneous, intravenous, intraperitoneal, or intramuscular administration.

In one aspect of the present invention, the composition is a formulation selected from a group consisting of: a tablet, capsule, spray, drop, solution, suspension, gel, ointment, lotion, cream, powder, transdermal patch, tampon, or a sponge.

It is an object of the present invention that the at least one phenylethanoid comprises oleocanthal. In another aspect, the at least one phenylethanoid is selected from a group consisting of: oleocanthal, tyrosol, hydroxytyrosol, and combinations thereof. In another aspect, the oleocanthal can be provided by including olive oil in the formulation as olive oil contains a significant level of oleocanthal.

It is another object of the present invention that the cannabinoid is selected from the group consisting of: cannabidiol (CBD), cannabidivarol (CBDV), cannabinol (CBN), cannabigerol (CBG), cannabivarol (CBV), cannabicyclol (CBL), tetrahydrocannabinol (THC), tetrahydrocannabinol-C4, (THC-C4), tetrahydrocannabivarin (THCV), 11-Hydroxy-Δ9-tetrahydrocannabinol, (11-OH-THC), 11-nor-9-Carboxy-Δ9-tetrahydrocannabinol, and combinations thereof.

It is another object of the present invention to provide a method of treating inflammation in a patient comprising administering to a patient in need thereof a therapeutically effective amount of a composition comprising at least one cannabinoid; and a phenylethanoid, such as oleocanthal.

It is another object of the present invention to provide a method for preparing a combination formulation having anti-inflammatory properties, the method comprising the steps of: providing at least one cannabinoid; providing at least one phenylethanoid; and combining the at least one cannabinoid and the at least one phenylethanoid to form a combination formulation; wherein said combination formulation is capable of reducing inflammation in an animal administered said combination formulation

BRIEF DESCRIPTION OF THE DRAWINGS

The present invention is further described in the detailed description which follows, in reference to the noted plurality of drawings by way of non-limiting examples of exemplary embodiments, in which like reference numerals represent similar parts throughout the several views of the drawings, and wherein.

Figure 1:
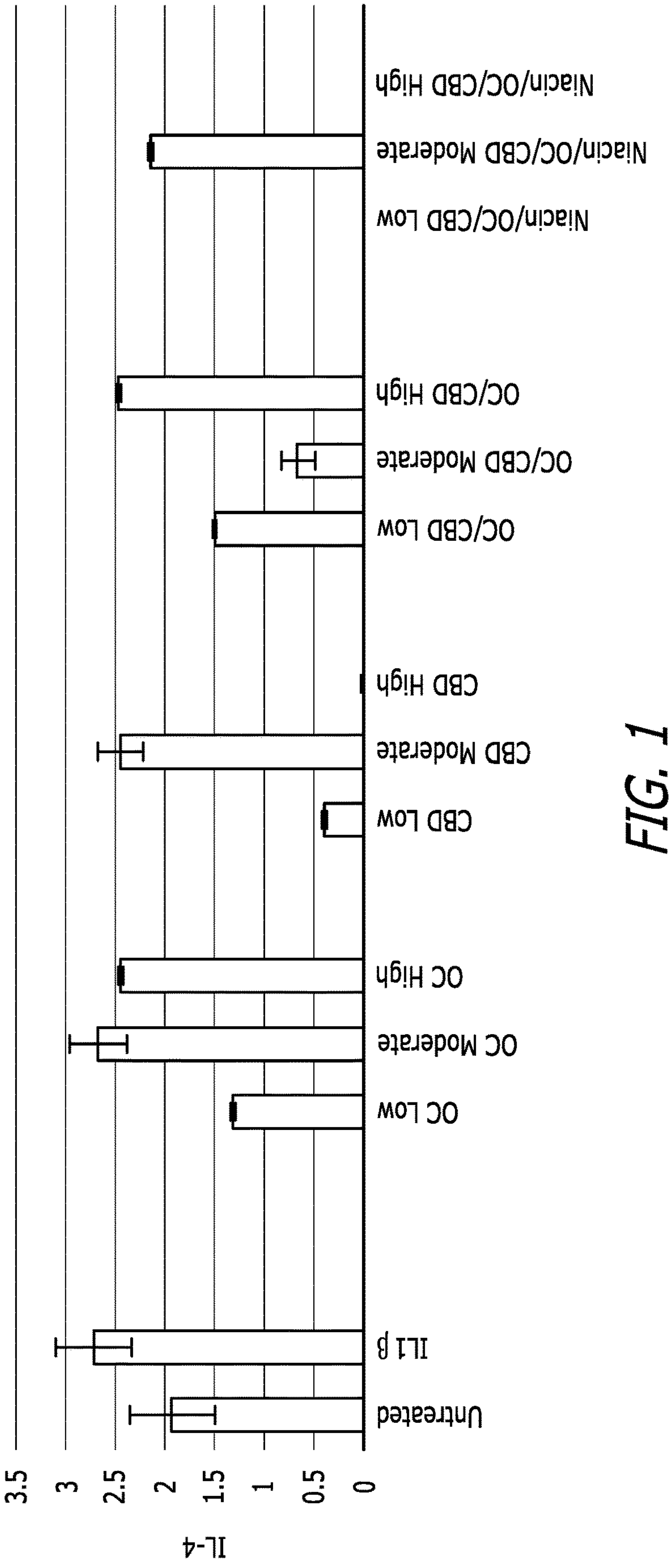
FIG. 1. depicts a chart showing interleukin 4 (IL-4) expression in pictograms per milliliter in chondrocyte cultures as a result of varying concentrations of individual and combination therapies.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the instant disclosure may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context Also, it is noted that individual embodiments may be described as a process which is depicted as a flowchart, a flow diagram, or a block diagram. Although a flowchart may describe the operations as a sequential process, many of the operations can be performed in parallel or concurrently. In addition, the order of the operations may be re-arranged.

In one embodiment of the present invention, a combination treatment of a formulation comprising at least one cannabinoid, such as CBD, and one or more phenylethanoid, such as oleocanthal or olive oil as a source of oleocanthal, the two ingredients capable of decreasing the secretion of inflammatory cytokines by chondrocytes in a synergistic manner. As known to one of skill in the art cytokines are small proteins of 5 to 20 Kilo-Daltons that are involved in cell signaling. The typical cytokines include: chemokines, interferons, interleukins, lymphokines and tumor necrosis factors. In the present disclosure the cytokines focused on are interleukins. Chondrocytes are the only cell type found in the lacunae of cartilage. They are responsible for synthesis of the collagen, proteoglycans and elastin fibers that make up cartilage.

Cannabinoids are chemical compounds found in the *cannabis* plant that interact with receptors in the brain and body to create various effects. *Cannabis* contains over 400 compounds including over 100 cannabinoids, which are aryl-substituted meroterpenes unique to the plant genus *cannabis*. The pharmacology of most of the cannabinoids is largely unknown but the most potent psychoactive agent, $\Delta^9$-tetrahydrocannabinol ($\Delta^9$-THC, or THC), has been isolated, synthesized and much studied due to its abundance and psychoactive attributes. Other plant-based cannabinoids include $\Delta^9$-tetrahydrocannabinolic acid, $\Delta^8$-THC, cannabigerol, cannabidiolic acid, and cannabidiol (CBD). These and other cannabinoids have additive, synergistic or antagonistic effects with THC and may modify its actions when *cannabis* products are consumed. For purposes of the present invention, the cannabinoid "CBD" is utilized, but is intended to be non-limiting, and can include all cannabinoids including combinations thereof.

To date, little research has been done around the medicinal uses of cannabinoids because the federal government currently classifies it as a Schedule I substance, which makes researching the plant extremely difficult. However, there is increasing evidence that cannabinoids, particularly cannabidiol (CBD), have beneficial uses, such as pain management, multiple sclerosis, epilepsy, Parkinson's disease, and post traumatic stress disorder (PTSD). Cannabinoids themselves are typically not strong enough for severe pain management like that from broken bones or post-surgical pain, but are effective for the management of chronic pain, and they are increasingly considered safer and less addictive than opiates and can also be taken as an alternative to nonsteroidal anti-inflammatory drugs (NSAIDs), such as Advil or Aleve.

Currently, there are few effective options to treating nerve pain other than Neurontin, Lyrica or highly sedating opiates. Patients have claimed certain cannabinoids allow them to resume the activities of daily living while not feeling overwhelmed by the side effects of powerful pharmaceutical drugs.

The FDA recently approved a drug called Epidiolex (derived from CBD) as a method to treat people with severe seizures. Some people show a large drop in the frequency of their seizures while taking the drug. Additionally, cannabinoids are known as an effective muscle relaxant, and many people with Parkinson's disease are convinced that it significantly lessens their tremors.

Other applications of cannabinoids include treatment of anorexia, nausea and weight loss. Certain cannabinoids, such as THC, reached the area of the brain that affects appetite and subsequently stimulate eating.

Research has shown that cannabinoids, such as CBD, are able to modulate the immune system and reduce convulsion and inflammatory pain in some animal studies by interacting with the endocannabinoid system, notably the CB1 and CB2 receptors, as well as other receptors, such as the TRPV1, glycine receptor and the like.

CBD has also been shown to reduce inflammatory pain in animal models, but again, not by interacting directly with the body's cannabinoid receptors. Rather, CBD appears to block inflammatory pain by interacting with another protein, the glycine receptor, which plays a critical role in transmitting pain signals from the body, through the spinal cord, and into the brain where pain is actually perceived.

CBD also acts on inflammation by decreasing oxidative stress in the body. Oxidative stress occurs when there is a disturbance between the production of free radicals and antioxidant defenses, resulting in inflammation or tissue damage. CBD possesses antioxidant properties, and has been shown to reduce oxidative stress and inflammation in the body following a potent chemotherapy treatment.

While multiple pathways are mediated by CBD's activity, it is a preferred embodiment of the present invention, that inflammation is itself mediated by chondrocytes. The chondrocyte is the only specialized cell type present in articular cartilage. They produce cytokines, growth factors, and extracellular matrix structural proteins to support and repair cartilage. Human chondrocytes in mature articular cartilage are loosely packed, post-mitotic and terminally differentiated cells making them sensitive to damage resulting in long-term consequences. Each chondrocyte is responsible for the turnover of extracellular matrix in its immediate vicinity. Pro-inflammatory cytokines can be secreted by chondrocytes resulting in feedback that modulates the degradation and synthesis of matrix proteins making up the cartilage. The development, maintenance, and repair of the extracellular matrix by chondrocytes dictates the health of joints. Dysregulated chondrocyte function leads to chronic pain and inflammation, ultimately leading to arthritis and permanent joint damage potentially requiring surgical repair. Superficial joints like the knees, ankles, feet, elbows, and hands are particularly receptive to topical penetrating medications to alleviate dysregulated inflammation and pain.

Oleocanthal is a phenylethanoid, or a type of natural phenolic compound found in olive oil and especially in extra-virgin olive oil. Phenylethanoids are a type of phenolic compounds characterized by a phenethyl alcohol structure. Tyrosol and hydroxytyrosol are other examples of such phenylethanoid compounds. Oleocanthal appears to be responsible for the burning sensation that occurs in the back of the throat when consuming such oil. Oleocanthal is a tyrosol ester and its chemical structure is related to oleuropein, also found in olive oil:

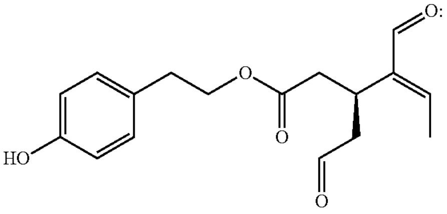

Oleocanthal

This olive oil derived phenolic compound has recently emerged as a potential therapeutic agent against a variety of diseases, including inflammation, cancer, neurodegenerative and cardiovascular diseases. Extra virgin olive oil (EVOO) in the Mediterranean region has long been associated with lower occurrences of certain chronic diseases, such as cancer incidence and cardiovascular mortality, as well as neurodegenerative dementias and Alzheimer disease. The major components of olive oil are the fatty acids, of which the monounsaturated fatty acid (MUFA) oleic acid represents from 55% to 83% of the total fatty acids, polyunsaturated fatty acids (PUFA) from 4% to 20%, and saturated fat acids (SFA) from 8% to 14%. Other minor components of olive oil constitute from 1% to 2% of the total content, and are divided into two groups: i) the unsaponifiable fraction that could be extracted with solvents after the saponification of the oil, which contains squalene, triterpenes, sterols, tocopherol, and pigments, and ii) the soluble fraction that includes phenolic compounds such as oleocanthal. Given the significant level of olecanthal in olive oil and especially EVOO, in the present specification and claims when olive oil is listed as a phenylethanoid it is meant that the source of the phenylethanoid, such as oleocanthal, is the olive oil. Thus, to add oleocanthal to a formulation one can add the purified compound or one can add olive oil, preferably EVOO, to provide the oleocanthal.

In one embodiment, the present invention provides a combination treatment of a formulation comprising at least one cannabinoid, such as CBD, and one or more phenylethanoid such as oleocanthal or olive oil, the two ingredients capable of decreasing the secretion of inflammatory cytokines by chondrocytes.

In one embodiment, the composition comprises an aqueous solution and one or more pharmaceutically acceptable excipients, additives, carriers or adjuvants. In another embodiment, the composition further comprises one or more excipients, carriers, additives, adjuvants, or binders in a tablet or capsule.

In another embodiment, the present invention may be in liquid, solid or semisolid dosage forms, including, but not limited to, emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

In another embodiment the composition is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, subligual, transdermal, pulmonary, rectal, or vaginal route. The composition is formulated in a dosage form selected from the group consisting of liquid, solid, gas, oral, pill, tablet, capsule, caplet, buccal, sub-lingual, orally-disintegrating, thin film, liquid solution, suspension, powder or liquid or solid crystals, pastes, inhalational, aerosol, inhaler, nebulizer, smoking, vaporizer, spray, syrup, parenteral, intradermal, intramuscular, intraosseous, intraperitoneal, intravenous, subcutaneous, topical, cream, gel, liniment or balm, lotion, ointment, drops, skin patch, vaginal, suppository, pessary, rectal and any combination thereof.

In another embodiment, the composition further comprises a hydrophobic component selected from the group consisting of: *cannabis* oil, borage oil, coconut oil, medium chain triglyceride (MCT) oil, cottonseed oil, soybean oil, safflower oil, sunflower oil, castor oil, corn oil, olive oil, palm oil, peanut oil, almond oil, sesame oil, rapeseed oil, peppermint oil, poppy seed oil, canola oil, palm kernel oil, hydrogenated soybean oil, hydrogenated vegetable oils, glyceryl esters of saturated fatty acids, glyceryl behenate, glyceryl distearate, glyceryl isostearate, glyceryl laurate, glyceryl monooleate, glyceryl, monolinoleate, glyceryl palmitate, glyceryl palmitostearate, glyceryl ricinoleate, glyceryl stearate, polyglyceryl 10-oleate, polyglyceryl 3-oleate, polyglyceryl 4-oleate, polyglyceryl 10-tetralinoleate, behenic acid, caprylyic/capric glycerides and any combination thereof.

The term "pharmaceutically acceptable carrier", "excipient", or "vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include but are not limited to saline, buffered saline, pectin, dextrose, water, glycerol, ethanol, and combinations thereof. The use of such media and agents for an active substance is well known in the art.

The pharmaceutically acceptable carrier may be selected from the group consisting of water, saline, cyclodextrin, glycerol, or combinations thereof. In one aspect, the pharmaceutically acceptable carrier is β-cyclodextrin. In another aspect, the pharmaceutically acceptable carrier is: α-cyclodextrin, β-cyclodextrin, γ-cyclodextrin, methylated β-cyclodextrin, hydroxypropyl- and hydroxyethyl-cyclodextrin (di) glucosyl- or (di)maltosyl-cyclodextrins, carboxymethyl-cyclodextrins, or sulfobutylether-β-cyclodextrin.

In another embodiment, preservatives may be used, referring to one or more of benzalkonium, benzalkonium chloride, potassium sorbate, benzyl alcohol, thimerosal (merthiolate), edetate disodium monobasic sodium phosphate, providone, di-basic sodium phosphate, disodium ETA, potassium phosphate monobasic, iodine, phenylcarbinol, sodium silicoaluminate, and the like. Indeed, other carriers, preservatives, buffers, moisturizers, or volatile oils or fragrances may be used in the composition of the present invention.

The composition of the present invention may further comprise a buffer system for increased stability/adjusting pH to reduce irritation. A preferred buffer system includes sodium chloride, calcium chloride, disodium hydrogen phosphate and calcium hydrogen phosphate, in a concentration sufficient to maintain the pH of the composition at a value inclusive of pH 5.5 to pH 8.5.

Example—Cytokine Expression Changes

A clonal derivative of ATCC-certified normal chondrocytes was used for a study to determine cytokine expression. The parent line was originally derived from costal cartilage of an adolescent female. The cell line used is C-28/I2 accession number CVCL_0187. The cells were immortalized via retroviral vector-mediated SV40 Large T antigen expression. Cells were confirmed negative for *mycoplasma* contamination and genotyped by STR analysis to verify cell identity. This cell line is widely used as a model for studying normal and pathological cartilage repair mechanisms and inflammation.

The cells were cultured at 37° C. with 5% $CO_2$, DMEM/F12 media supplemented with 10% heat-inactivated fetal bovine serum. Antimicrobials were not added to the media. Cells were maintained between 40 and 80% confluency to avoid terminal differentiation. Cells used for the experiments had been passaged no more than ten times prior to each experiment.

Stock solutions of cannabidiol (CBD, mol. wt 314.47, isolate), niacin/nicotinic acid (Sigma, ≥99.5% HPLC, mol. wt: 123.11), and oleocanthal (Oleolive, ≥98% HPLC, mol wt: 304.34) were made up in DMSO to final concentrations of 50 millimolar (mM), 150 mM, 150 mM, and 50 mM respectively. Stock solutions were aliquoted to minimize freeze-thaw cycles and stored at −20° C. Recombinant Human IL-1β and IL-6 (PeproTech, ≥98% HPLC) were reconstituted in sterile cell culture grade water to 0.1 mg/ml, aliquoted, and stored at −20° C. Lipopolysaccharide (LPS, Enzo, ≥98% HPLC) from *E. coli* EH100 (Ra) was reconstituted in sterile cell culture grade water to 1.0 mg/ml and stored at 4° C.

To identify cytokine expression changes in chondrocytes treated with cannabidiol or oleocanthal, either alone or in combination with an additional combination including cannabidiol, oleocanthal and niacin, cells arrayed in 24-well cell culture plates were grown to 70% confluency, which is approximately ~$5.0\times10^4$ cells per well, and then were treated for 24 hours under each condition in the absence of serum. Three wells were utilized per sample condition. Cytokines secreted over time by the cells under different treatments accumulate in the cell culture media, this media is called conditioned media. Conditioned media was collected under sterile conditions, centrifuged at 3,000×g for 5 minutes at 4° C., and the supernatant was diluted to the appropriate volume. Lysates were taken for each sample to normalize resulting data based on cell number. Samples were shipped on dry ice for to a third party for cytokine array analysis. Cytokine arrays provided by and analyzed by a third party company were used to detect distinct pro-inflammatory cytokines for each sample provided. Assays were performed using the Bio-Plex 200 system (BIO-RAD LABORATORIES). Assay sensitivities for each analyte/cytokine ranged from 0.11 to 3.25 picogram/milliliter. Raw data values were provided with corresponding standard curve values for each analyte.

A series of pilot studies were performed to design the final full-scale experiment. First, a toxicity screen for each test compound was performed to establish maximum tolerable concentrations in this model system. Second, assays were run to establish the optimal means of inducing a pro-inflammatory state in the cell culture system. Third, conditions were tested to set the most favorable dilution scheme in order to maintain samples within the linear range of detection for each analyte. To establish the test concentrations for each test compound, chondrocytes were treated with a serial dilution of each compound, for 24 and 48 hours under serum free conditions. Oleocanthal or CBD were tested at two-fold dilutions down from a concentration of 50 micromolar (μM). The maximum tolerable concentration at 24 hours post-treatment for oleocanthal, CBD, niacin, and nicotinamide ribose were 6 μM, 6 μM, 1 mM and 1 mM, respectively.

Experiments were then performed to optimize the model of a pro-inflammatory state. Chondrocytes were treated with a range of concentrations of IL-6, IL-10, LPS, or combinations of each in order to stimulate the cells to produce pro-inflammatory cytokines. The cells were treated in the presence or absence of serum in the media, for 24 or 48 hours. Samples were collected for each of these conditions in varying combinations and shipped for third party analysis to detect the levels of different cytokines present in the conditioned media. From the results at least 8 of the 14 cytokines were detected in the array produced by the cells under optimal conditions. These optimal conditions were IL-10 stimulation alone, in the absence of serum, for 24 hours. So for the date presented in the Figures the 24 hour treatments were: control no additions, IL1β alone, IL1β plus the indicated compound(s).

For the purposes of the present invention, the levels "Low", "Moderate", and "High" relate to the dosage of the treatment of each replicate in the provided example, in accordance with Table 1, below, correlating with the data set forth in the Figures regarding the exemplary embodiment.

TABLE 1

Concentration/Dosage levels for Low, Moderate, and High concentrations.

| | Final DMSO | IL1β (ng/ml) | Oleocanthal (μM) | Cannabidiol (μM) | Niacin (μM) |
|---|---|---|---|---|---|
| Untreated | <.1% | 10 | | | |
| IL1β | <.1% | 10 | | | |

TABLE 1-continued

Concentration/Dosage levels for Low, Moderate, and High concentrations.

| | Final DMSO | IL1β (ng/ml) | Oleocanthal (μM) | Cannabidiol (μM) | Niacin (μM) |
|---|---|---|---|---|---|
| OC low | <.1% | 10 | 0.67 | | |
| OC moderate | <.1% | 10 | 2.00 | | |
| OC high | <.1% | 10 | 6.00 | | |
| CBD low | <.1% | 10 | | 0.67 | |
| CBD moderate | <.1% | 10 | | 2.00 | |
| CBD high | <.1% | 10 | | 6.00 | |
| OC/CBD low | <.1% | 10 | 0.67 | 0.67 | |
| OC/CBD moderate | <.1% | 10 | 2.00 | 2.00 | |
| OC/CBD high | <.1% | 10 | 6.00 | 6.00 | |
| Niacin/OC/CBD low | <.1% | 10 | 0.67 | 0.67 | 100.00 |
| Niacin/OC/CBD moderate | <.1% | 10 | 2.00 | 2.00 | 300.00 |
| Niacin/OC/CBD high | <.1% | 10 | 6.00 | 6.00 | 900.00 |

To ensure the maximum amount of information possible from the present example, a second pilot assay was performed comparing standard and high sensitivity arrays at a series of sample dilutions. This was necessary to ensure analytes were within the optimal linear detection range. It was determined that two-fold dilutions of each sample should be assayed on the high-sensitivity arrays.

The results of the present example are set forth in the Figures, the data is shown in picograms per milliliter. From the above described example there are multiple principle findings that confirm the tested compounds act additively or synergistic in combination to repress production of pro-inflammatory cytokines by chondrocytes. In one aspect, Moderate and High concentrations of CBD and niacin act synergistically in combination to repress GM-CSF production (see FIG. 2). (SHOULD READ) In one aspect, a Moderate level of CBD alone greatly reduced the generated amount of IL13, see FIG. 2. In another aspect the combination of a High level of CBD and oleocanthal acted synergistically to dramatically reduce the level of IL13 produced, see FIG. 2.

In one embodiment, moderate concentrations of CBD and oleocanthal act synergistically in combination to repress IL-4 production (see FIG. 1).

Turning to the Figures, FIG. 1. depicts a chart showing the synergistic effect of combination therapies on pro-inflammatory IL-4 expression compared to non-combination therapies. Results shown include administration of various levels of CBD, oleocanthal, and both in combination, including Low, Moderate, and High levels of administration, as further defined herein. The results show that a combination of Moderate levels of CBD with oleocanthal lead to a synergistic reduction of IL-4 expression.

Figure 2:
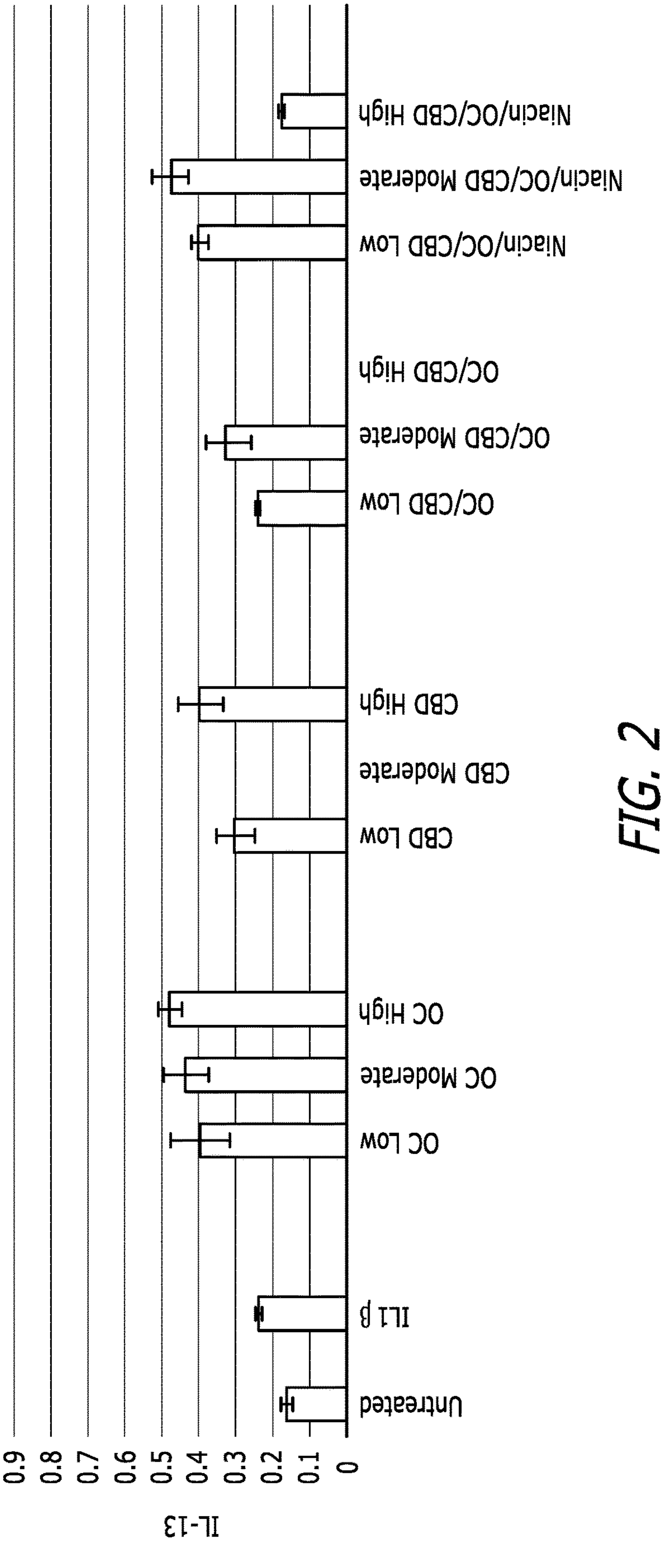
FIG. 2 depicts a chart showing interleukin 13 (IL-13) expression in pictograms per milliliter in chondrocyte cultures as a result of varying concentrations of individual and combination therapies.

FIG. 2 further presents data showing Low, Moderate and High concentrations of individual and combination therapies and the corresponding effect on IL-13 expression. From the results one sees that a High combination treatments of CBD and oleocanthal showed an increased, synergistic anti-inflammatory effect of a reduction in IL-13 production.

From the above described examples there are multiple principle findings that confirm the tested compounds act additively or synergistic in combination to repress production of pro-inflammatory cytokines by chondrocytes. In one aspect, Moderate and High concentrations of CBD and oleocanthal act synergistically in combination to repress IL-4 and IL-13 production, respectively (see FIGS. 1-2). It is believed that the results are applicable to treatment of all animals, including humans, pet animals, zoo animals, livestock and farm stock animals. As discussed above it is preferred that the molar ratio of the at least one cannabinoid to the at least one phenylethanoid is between 10:1 to 1:10; more preferably 5:1 to 1:5 and most preferably from 1:1. In terms of the amount of cannabinoid in a dosage formulation it is preferred that this ranges from 0.1 to 100.0 milligrams of cannabinoid per dosage with a corresponding amount of the at least one phenylethanoid. If the phenylethanoid is olecanthal this means approximately 0.096 to 100 milligrams of olecanthal per dosage.

It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

REFERENCES

1. Antiseizure properties of cannabidiol (CBD) are attenuated in the absence of transient receptor potential vanilloid 1 (TRPV1) receptors (553.004) Benjamin J. Whalley, Royston A. Gray, Colin G. Stott, Nicholas A. Jones *Neurology* April 2018, 90 (15 Supplement) S53.004.
2. Costa B1, Trovato A E, Comelli F, Giagnoni G, Colleoni M. The non-psychoactive *cannabis* constituent cannabidiol is an orally effective therapeutic agent in rat chronic inflammatory and neuropathic pain. *Eur J Pharmacol.* 2007 Feb. 5; 556(1-3):75-83. Epub 2006 Nov. 10.
3. Covas M. I., Konstantinidou V., Fitó M. Olive Oil and Cardiovascular Health. *J. Cardiovasc. Pharmacol.* 2009; 54:477-482. doi: 10.1097/FJC.0b013e3181c5e7fd.
4. Peyrot des Gachons C., Uchida K., Bryant B., Shima A., Sperry J. B., Dankulich-Nagrudny L., Tominaga M., Smith III A. B., Beauchamp G. K., Breslin P. A. S. Unusual Pungency from Extra-Virgin Olive Oil Is Attributable to Restricted Spatial Expression of the Receptor of Oleocanthal. *J. Neurosci.* 2011; 31:999-1009. doi: 10.1523/JNEUROSC.1374-10.2011.
5. Sofi F., Cesari F., Abbate R., Gensini G., Casini A. Adherence to Mediterranean diet and health status: meta-analysis. *Br. Med. J.* 2008; 337:a1344.3. doi: 10.1136/bmj.a1344.
6. Ji H. F., Zhang H. Y. Multipotent natural agents to combat Alzheimer's disease. Functional spectrum and structural features. *Acta Pharmacol*. Sin. 2008; 29:143-151. doi: 10.1111/j.1745-7254.2008.00752.x.
7. Li W., Sperry J. N., Crowe A., Trojanoswki J. Q., Smith III A. B., Lee V. M. Y. Inhibition of tau fibrillization by oleocanthal via reaction with the amino groups of tau. *J. Neurochem.* 2009; 110:1339-1351. doi: 10.1111/j.1471-4159.2009.06224.x.
8. Smith III A. B., Sperry J. B., Han Q. Syntheses of (−)-Oleocanthal, a Natural NSAID Found in Extra Virgin Olive Oil, the (−)-Deacetoxy-OleuropeinAglycone, and Related Analogues. *J. Org. Chem.* 2007; 72:6891-6900. doi: 10.1021/jo071146k.

What is claimed is:

1. A composition for treatment of inflammatory conditions in an animal, said composition comprising:

at least one cannabinoid; and at least one phenylethanoid;

wherein said composition is capable of having an anti-inflammatory effect when administered to an animal, and wherein the at least one phenylethanoid comprises oleocanthal.

2. The composition of claim 1, wherein the molar ratio of the at least one cannabinoid and the at least one phenylethanoid is between 10:1 and 1:10.

3. The composition of claim 1, wherein the molar ratio of the at least one cannabinoid and the at least one phenylethanoid is between 5:1 and 1:5.

4. The composition of claim 1, wherein the molar ratio of the at least one cannabinoid and the at least one phenylethanoid is substantially 1:1.

5. The composition of claim 1, wherein said composition is suitable for administration selected from a group consisting of: oral administration, topical administration, mucosal administration, pulmonary administration, subcutaneous administration, intravenous administration, intraperitoneal administration, suppository administration, and intramuscular administration.

6. The composition of claim 1, wherein said composition is a formulation selected from a group consisting of: a tablet, capsule, spray, drop, solution, suspension, gel, ointment, lotion, cream, powder, transdermal patch, tampon, or a sponge.

7. The composition of claim 1, wherein the at least one phenylethanoid is selected from the group consisting of: olive oil, oleocanthal, tyrosol, hydroxytyrosol, and combinations thereof.

8. The composition of claim 1, wherein the cannabinoid is cannabidiol (CBD).

9. The composition of claim 1, wherein the cannabinoid is selected from the group consisting of: cannabidiol (CBD), cannabidivarol (CBDV), cannabinol (CBN), cannabigerol (CBG), cannabivarol (CBV), cannabicyclol (CBL), tetrahydrocannabinol (THC), tetrahydrocannabinol-C4, (THC-C4), tetrahydrocannabivarin (THCV), 11-Hydroxy-49-tetrahydrocannabinol, (11-OH-THC), 11-nor-9-Carboxy-Δ9-tetrahydrocannabinol, and combinations thereof.

10. A method for preparing a combination formulation having anti-inflammatory properties, the method comprising the steps of:

providing at least one cannabinoid;

providing at least one phenylethanoid, wherein the at least one phenylethanoid comprises oleocanthal; and combining the at least one cannabinoid and the at least one phenylethanoid to form a combination formulation;

wherein said combination formulation is capable of reducing inflammation in an animal administered said combination formulation.

11. The method of claim 10, wherein a molar ratio of the at least one cannabinoid and the at least one phenylethanoid in the combination formulation is between 10:1 and 1:10.

12. The method of claim 10, wherein a molar ratio of the at least one cannabinoid and the at least one phenylethanoid in the combination formulation is between 5:1 and 1:5.

13. The method of claim 10, wherein a molar ratio of the at least one cannabinoid and the at least one phenylethanoid in the combination formulation is substantially 1:1.

14. The method of claim 10, wherein said combination formulation is suitable for administration selected from a group consisting of: oral administration, topical administration, mucosal administration, pulmonary administration, subcutaneous administration, intravenous administration, intraperitoneal administration, suppository administration, and intramuscular administration.

15. The method of claim 10, wherein said combination formulation is a formulation selected from the group consisting of: a tablet, capsule, spray, drop, solution, suspension, gel, ointment, lotion, cream, powder, transdermal patch, tampon, or a sponge.

16. The method of claim 10, wherein the at least one phenylethanoid is selected from a group consisting of: olive oil, oleocanthal, tyrosol, hydroxytyrosol, and combinations thereof.

17. The method of claim 10, wherein the cannabinoid is cannabidiol (CBD).

18. The method of claim 10, wherein the cannabinoid is selected from the group consisting of: cannabidiol (CBD), cannabidivarol (CBDV), cannabinol (CBN), cannabigerol (CBG), cannabivarol (CBV), cannabicyclol (CBL), tetrahydrocannabinol (THC), tetrahydrocannabinol-C4, (THC-C4), tetrahydrocannabivarin (THCV), 11-Hydroxy-49-tetrahydrocannabinol, (11-OH-THC), 11-nor-9-Carboxy-Δ9-tetrahydrocannabinol, and combinations thereof.

* * * * *